United States Patent
Hanson et al.

(10) Patent No.: US 8,911,491 B2
(45) Date of Patent: *Dec. 16, 2014

(54) METHODS AND APPARATUS FOR TREATMENT OF ANEURYSMS ADJACENT BRANCH ARTERIES INCLUDING BRANCH ARTERY FLOW LUMEN ALIGNMENT

(75) Inventors: Curtis Hanson, San Marcos, CA (US); Scott Cook, New Farm (AU); Joseph Lessar, Coon Rapids, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1675 days.

This patent is subject to a terminal disclaimer.

(21) Appl. No.: 11/219,329

(22) Filed: Sep. 2, 2005

(65) Prior Publication Data

US 2007/0055360 A1 Mar. 8, 2007

(51) Int. Cl.
*A61F 2/06* (2013.01)

(52) U.S. Cl.
USPC ....... 623/1.35; 623/1.11; 623/1.12; 623/1.13; 623/1.14; 623/1.15; 623/1.16; 623/1.17; 623/1.18; 623/1.3; 623/1.21; 623/1.33; 606/108; 606/191; 606/194; 606/195; 606/198

(58) Field of Classification Search
USPC ............. 623/1.11, 1.15–1.16, 1.35–1.36, 1.1, 623/1.13, 1.23, 1.21, 1.18; 606/191, 194, 606/195, 198, 108

See application file for complete search history.

(56) References Cited

U.S. PATENT DOCUMENTS

| | | | | |
|---|---|---|---|---|
| 5,254,133 A | * | 10/1993 | Seid | 606/215 |
| 5,527,355 A | * | 6/1996 | Ahn | 623/1.36 |
| 5,607,444 A | * | 3/1997 | Lam | 606/194 |
| 5,683,450 A | * | 11/1997 | Goicoechea et al. | 606/194 |
| 6,030,414 A | * | 2/2000 | Taheri | 623/1.1 |
| 6,676,691 B1 | * | 1/2004 | Hosny | 623/1.11 |
| 6,695,877 B2 | * | 2/2004 | Brucker et al. | 623/1.16 |
| 6,908,477 B2 | * | 6/2005 | McGuckin et al. | 623/1.11 |
| 6,949,121 B1 | * | 9/2005 | Laguna | 623/1.35 |
| 7,425,219 B2 | * | 9/2008 | Quadri | 623/1.35 |
| 2002/0193872 A1 | * | 12/2002 | Trout et al. | 623/1.34 |
| 2004/0133268 A1 | * | 7/2004 | Davidson et al. | 623/1.35 |
| 2004/0176835 A1 | * | 9/2004 | Vrba | 623/1.16 |
| 2005/0113905 A1 | * | 5/2005 | Greenberg et al. | 623/1.16 |
| 2005/0171598 A1 | * | 8/2005 | Schaeffer | 623/1.35 |

FOREIGN PATENT DOCUMENTS

| | | | | | |
|---|---|---|---|---|---|
| WO | WO 0222055 | * | 3/2002 | | A61F 2/06 |
| WO | WO 2005034810 A1 | * | 4/2005 | | A61F 2/06 |

* cited by examiner

*Primary Examiner* — Vy Q Bui

(57) ABSTRACT

A stent graft extends in a flow lumen to span a defective portion of the flow lumen and seal the defective portion from further blood contact. The stent graft includes a pair of apertures, from which extensions project into the renal arteries to seal the passage of blood into the renal arteries from the abnormality. The apertures are larger than the opening of the renal arteries, such that the apertures need not be centered with the renal arteries to enable placement of the extensions. The aperture opening and side branch extensions contain hook and loop structures to provide a variably positionable seal of the aperture opening.

15 Claims, 17 Drawing Sheets

METHODS AND APPARATUS FOR TREATMENT OF ANEURYSMS ADJACENT BRANCH ARTERIES INCLUDING BRANCH ARTERY FLOW LUMEN ALIGNMENT

FIELD OF THE INVENTION

The field of the invention is the treatment of vascular abnormalities. More particularly, the field of the invention is the treatment of vascular abnormalities by placing an excluding device in a blood vessel to exclude or bypass an abnormality, including placing such an excluding device in an area near one or more branch vessels so as to bypass the abnormality, but not occlude the branch vessel.

BACKGROUND OF THE INVENTION

"Aortic aneurysm" is the term used to describe a vascular abnormality condition where a segment of the aorta is dilated to a diameter greater than its original diameter. Aneurysms can occur in virtually any region of the vasculature including the aorta in the abdominal and thoracic regions. Aortic aneurysms are caused by hardening of the arteries (atherosclerosis), high blood pressure (hypertension), genetic disposition such as Marfan's Syndrome, trauma, or less common disorders. Atherosclerosis is the most common cause.

Where dilation of the aorta meets or exceeds 50% of the original aortic diameter, i.e., where the diameter of the aorta is 150% of the original or expected diameter, intervention generally is deemed necessary. Without intervention, the aneurysm may continue to expand, leading to the possibility of tearing or rupture of the aorta, and death. Intervention includes techniques such as open repair which involves replacement of the aorta with a synthetic lumen which is sewn to the two ends of the still viable aorta after the aneurysmal portion has been opened or surgically removed, or, less invasively, by the endovascular placement of an exclusion device such as a stent graft across the aneurysmal site. The stent graft is a tubular member designed to provide a conduit enabling blood flow through the aorta without allowing the systemic pressure of the blood to further stretch the aneurysm. For this intervention to be successful, the stent graft must extend across the weakened blood vessel wall so that the opposed ends engage and seal against healthy blood vessel tissue on either side of the aneurysm.

A stent graft includes a stent framework, which provides structural support of the stent graft in a tubular configuration once deployed at a vascular location, and a graft portion, comprising an excluding material, which is sewn or otherwise attached to the stent frame and which provides a relatively fluid-tight conduit for blood flow through the stent graft and past the aneurysm site. Placement of a stent graft can be performed without a chest incision, by using specialized catheters that are introduced through arteries usually at a location in a leg adjacent to the groin.

The aorta has numerous arterial branches. For example, the abdominal aorta includes the superior mesentery artery, the celiac trunk and the renal arteries. The proximity of an aneurysm to a branch artery may limit the use of an excluding device such as a tubular stent graft, as the main body or ends of the tubular stent graft may occlude or block the branch arteries due to the need to position the stent graft to seal against a healthy, i.e., non diseased or dilated, portion of the artery wall. There may be an inadequate length of healthy tissue for the stent graft to seal against in the area between the aneurysmal region of the aorta and the location of the branch arteries or even if the stent graft initially is located without blocking a branch artery, there still is a risk of migration of the exclusion device to a position where it may partially or fully block a branch artery. Additionally, where multiple branch arteries are present adjacent to the aneurysm, the ability to position a stent graft so as not to occlude any of the branch arteries may be problematic. Furthermore, where a stent graft needs to be located in an aorta and span a branch artery, the stent graft must be specifically configured to the particular patient's anatomy, i.e., apertures to enable blood flow into the branch arteries must be provided at specific locations in the tubular wall which align, when the stent graft is deployed, with the branch artery locations. Therefore, there is a desire in the art to achieve a greater success of aneurysm repair and healing, and in particular, mechanisms and methods to enable stent grafting or the placement of other exclusion devices adjacent to branch vessels in aneurysmal locations with minimal need to customize the stent graft for a specific patient, but still enable placement of the stent graft across a branch artery while providing a sealed path for blood flow into the branch artery.

SUMMARY OF THE INVENTION

Embodiments according to the present invention address aneurysm repair and in situ positional stability of a device used for aneurysm repair. Specifically, embodiments according to the present invention provide methods and apparatus for use in the treatment of aneurysms located near branch vessels using an exclusion device such as a stent graft Thus, in one embodiment according to the invention there is provided an exclusion device useful for implantation in an aneurysmal site in a blood vessel having a branch vessel near the aneurysmal site comprising: a main body having at least one aperture therein alignable with the opening of a branch artery, wherein a secondary flow lumen creating structure is receivable in a sealing relationship with the aperture and extendable therefrom into sealing engagement with the branch artery, and the aperture is larger than, and overlies, the opening of the branch artery from the aorta or artery in which the main body of the stent graft is deployed. In one aspect, the secondary flow lumen creating structure is a tubular structure having a first end received in the aperture and a second end extending into the branch artery, and the circumference of the first end is smaller than that of the aperture.

In a further aspect, the first end includes, about its circumference, an attachment device for attachment of the secondary flow lumen creating structure to the main body of the stent graft. The attachment device may include one of either a plurality of hooks or a plurality of loops of a hook-loop connection system, and the surface of the main body adjacent to the aperture includes the complimentary structure of the hook-loop connection system (i.e., either a plurality of hook or loops), such that the attachment device, when pressed against the area of the main body adjacent to the aperture as the secondary flow lumen creating structure is extended into the aperture, causes the hooks and loops to adjoin, and at least a portion of the hooks engage through the loops to secure the attachment device against the main body of the flow lumen.

In another aspect, the branch artery is a renal artery, and the main body of the exclusion device extends across both renal artery openings (apertures) from the aorta, and the exclusion device, adjacent to the apertures is not in direct contact with the aorta wall, such that the secondary flow lumens form renal artery extensions which span the gaps between the body of the exclusion device and the ostiums of the renal arteries to provide sealed passages for flow of blood through the exclusion device and secondary flow lumens to provide flow into the renal arteries without allowing such flow to leak into the sealed off aneurysmal region. In a further aspect, the exclusion device is configured as a stent graft, having a stent framework and a graft material formed thereover and attached thereto.

The exclusion device having side branching openings (or apertures) is deployed into an aneurysmal flow lumen, such as within an aorta, where the openings (ostiums) of branch arteries are present and must be spanned by the exclusion device. The exclusion device is deployed, from a catheter, to position its opposed ends such that the aneurysmal portion of the aorta is excluded from blood flow, except for the apertures. The apertures are configured such that the openings of the branch arteries align within the outward imaginary cylindrical projection of the apertures. Each aperture is larger, in circumference, than the adjacent branch artery opening (ostium) from the aorta. A secondary flow lumen device is then deployed via an intravascular catheter into the aperture and extends from the aperture into the adjacent branch artery. The secondary flow lumen device is smaller in circumference than the aperture. To secure the secondary flow lumen device in the aperture, the secondary flow lumen device is attached at the end thereof received in the aperture to an attachment member which, during deployment, is pressed against the inner wall of the main body of the exclusion device adjacent to the aperture to seal against the main body as the secondary flow lumen device creates a passage that spans the gap between the main body aperture and the ostium of the renal artery.

BRIEF DESCRIPTION OF THE DRAWINGS

A description of embodiments according to the invention may be had by reference to the present specification and appended drawings.

DETAILED DESCRIPTION

Methods and apparatus for stabilizing and treating an aneurysm include deploying an exclusion device, such as a stent graft, in the flow lumen of a blood vessel to span the aneurysmal location and seal off the aneurysmal location of the blood vessel from further blood flow while acting as a conduit to direct blood flow past the aneurysmal site. In the case of an aneurysm near a branch artery, methods and apparatus for treatment include positioning an endovascular stent graft across the aneurysmal site, where the stent graft includes a body having a generally cylindrical wall with generally opposed apertures, where separate individual inserts are disposed within each aperture to extend sealingly into the exclusion device and sealingly into a branch vessel. An aperture is sized such that its circumference exceeds that of the exit of the branch vessel from the blood vessel, and the insert includes a tubular structure having a circumference smaller than that of the aperture which provides the flow conduit extendable into the branch vessel, and a base which is larger in circumference than the aperture and sealingly engages against the wall of the stent graft about the periphery of the aperture. Thus, the insert may be positioned with some positionable variance, vis-à-vis the aperture, to enable the use of the exclusion device with limited patient customization.

In addition to providing a flow lumen into the branch vessel, the inserts provide additional positional stability for the deployed stent graft and span any gap between the stent graft and the adjacent aorta wall. Thus, in an aortic aneurysm, the stent graft excludes the weakened vessel wall at the aneurysmal site from further exposure to blood flowing through the aorta, but, as a result of side branch apertures, allows blood to flow from the aorta to the branch artery(ies), even when the main body of the stent graft extends across branch artery(ies)' openings. Inserts are provided to fit sealingly into each aperture and further extend sealingly into the branch vessels, thereby preventing leakage of blood from the branch arteries into the region between the stent graft and the weakened blood vessel wall at the aneurysmal location.

Figure 1:
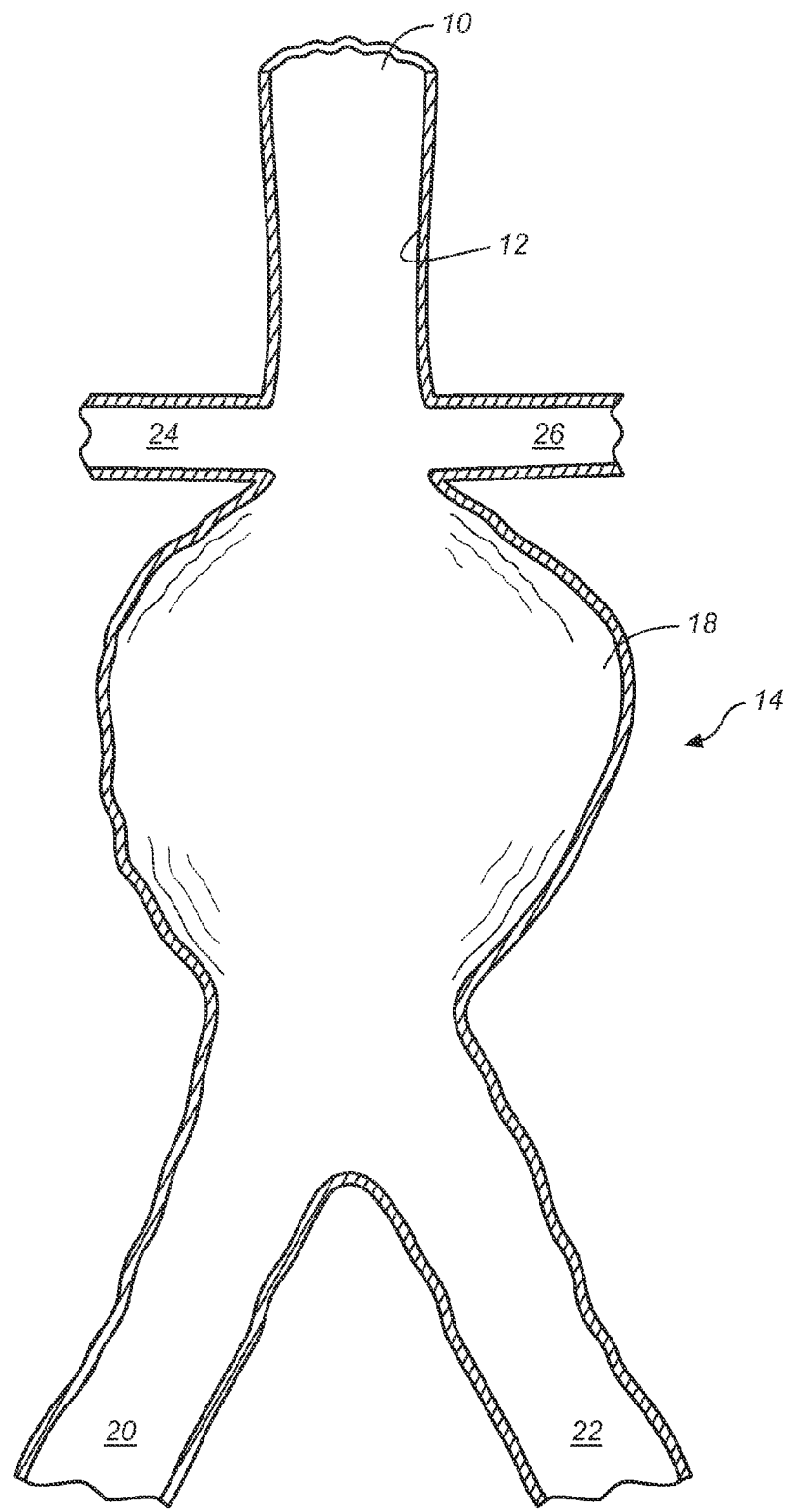
FIG. 1 is an artist's rendering of a cross section of an abdominal aorta showing an aneurysm near the renal artery branch locations.

Referring initially to FIG. 1, there is shown an aneurysm of the abdominal aorta 10, such that the aorta 10 is enlarged at an aneurysmal location 14 at which the aorta wall 12 is distended and stretched. The distended and stretched aneurysmal location 14 forms an aneurysmal bulge or sac 18. If left untreated, the aneurysmal portion of the aorta wall 12 may continue to deteriorate, weaken, and eventually tear or burst. In the aorta 10 shown in FIG. 1, the aneurysmal sac 18 is located adjacent to, and on the upstream (blood flow direction) side of, the branching of the aorta 10 into the right iliac artery 20 and left iliac artery 22, and downstream of the opening to the renal arteries 24, 26. Dilation of the aorta 10 in this FIG. 1 begins just above the renal arteries 24, 26 and the aorta 10 is dilated much more immediately below the renal artery 24, 26 locations. Thus, to exclude the aneurysmal sac 18, the excluding device must span the renal arteries 24, 26, and, seal against the aorta wall 12 at a location upstream of the renal arteries 24, 26.

Figure 2:
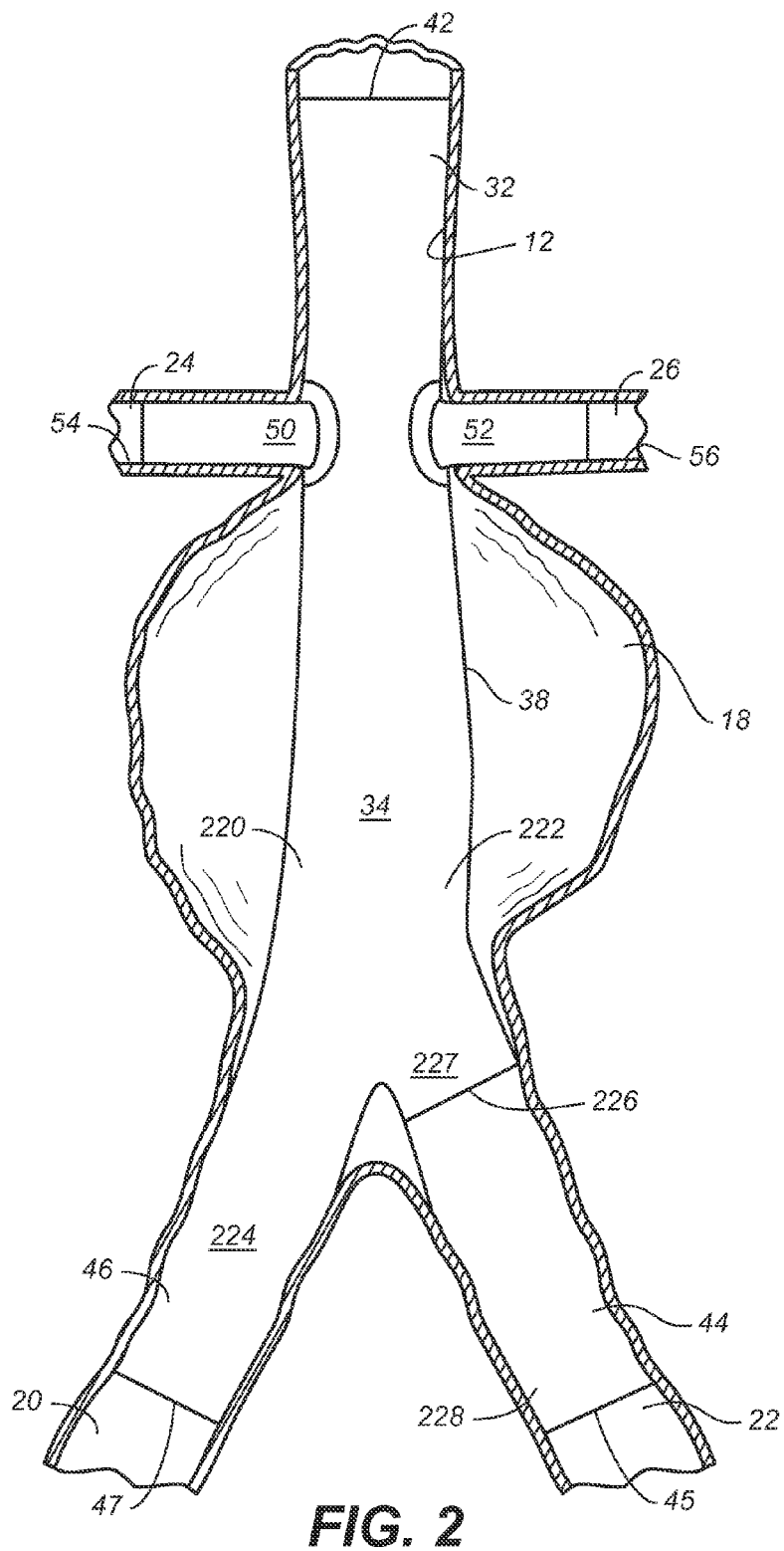
FIG. 2 is a view of the abdominal aortic aneurysm of FIG. 1 having an excluding device deployed therein.

Referring now to FIG. 2, a stent graft 32 is shown deployed in the aneurysmal aorta 10 to exclude the aneurysmal sac 18 and sealingly engage against the aorta wall 12 at locations on either side of the aneurysmal sac 18. Stent graft 32 generally includes a body 34 formed of graft material 38 and a stent framework 40 (Shown in FIG. 9) as will be further described herein, and includes a first end 42 deployed upstream from a blood flow perspective, from the openings for the renal arteries 24, 26 and at its opposite end, bifurcates into left and right iliac leg portions 44, 46, terminating in open left and right ends 45, 47 respectively. Stent graft 32, when deployed, sealingly engages against the inner walls of the iliac arteries 20, 22 by engagement of the stent graft 32 against the arterial walls of the iliac arteries 20, 22 adjacent to the ends 45, 47 of the legs 44, 46 thereof, and extends therefrom to a position upstream of the openings for the renal arteries 24, 26; and there seals against the artery wall 12. Thus, the stent graft 32 provides exclusion of the aneurysmal sac 18 from fresh blood supply while providing a blood flow bypass of the aneurysmal sac 18 through the hollow interior of the stent graft 32. To allow blood flow from the aorta 10 into the renal arteries 24, 26, and simultaneously seal off the adjacent aneurysmal sac 18, the stent graft 32 also includes a pair of generally opposed branch opening secondary flow lumen devices configured as renal extensions 50, 52, which extend across any gap between the stent graft 32 and the aorta wall 12 and into sealing engagement against the walls 54, 56 of the renal arteries 24, 26 while allowing fluid flow from the hollow interior of the body 34 therethrough.

Figure 3:
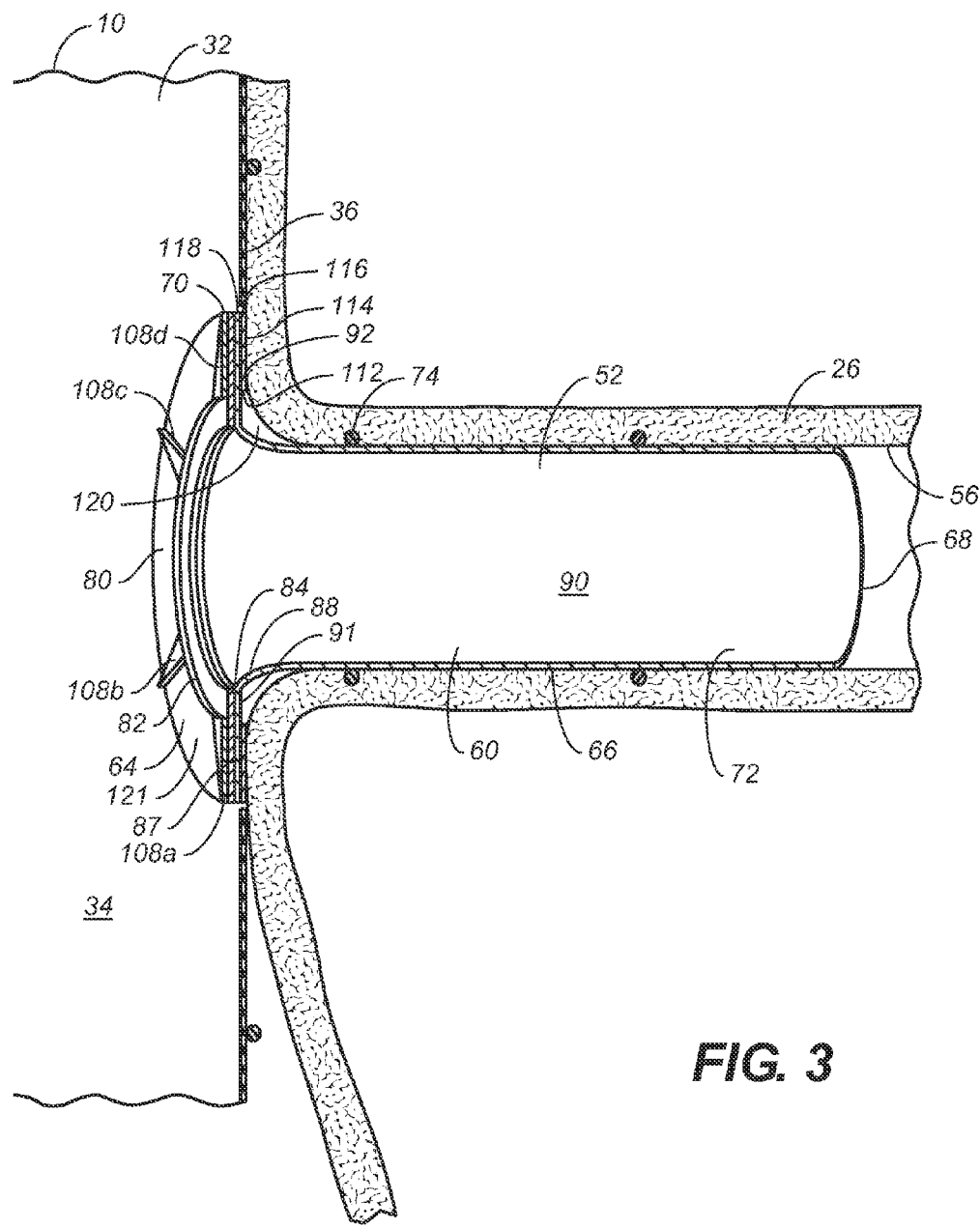
FIG. 3 is a cross sectional view of a renal extension extending from the main body of an excluding device deployed in an abdominal aorta and extending into an adjacent renal artery.
Figure 4:
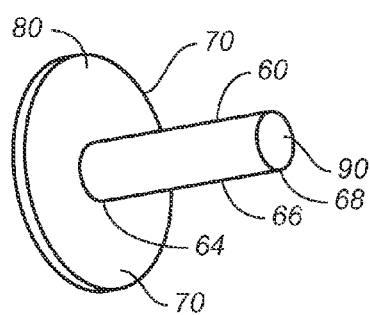
FIG. 4 is an isometric view of the renal extension shown in FIG. 3.
Figure 5:
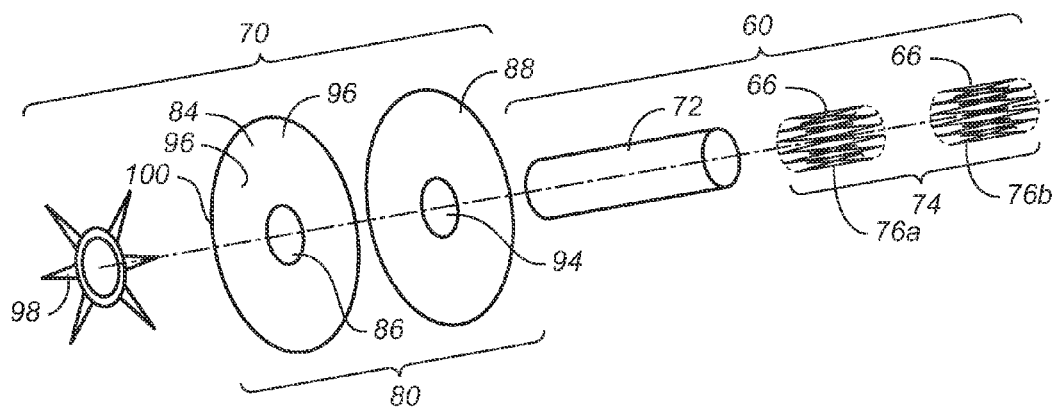
FIG. 5 is a three dimensional exploded view of the renal extension of FIG. 4.

Referring now to FIGS. 3 to 7, the structure and arrangement of the renal extensions 50, 52 and their securement to the body portion 34 of the stent graft 32 is shown. In this embodiment, the renal extensions 50, 52 (only extension 52 shown in FIGS. 3 to 7) are configured to include a tubular flow conduit 90 which generally extend from an graft aperture 118 in the body portion 34 and into the renal arteries 24, 26 (only artery 26 shown in FIG. 3) and are biased against the inner wall 54, 56 (only wall 56 shown in FIG. 3) thereof by use of a biasing member, such as a stent as will be discussed further herein, and are also secured by attachment of an annular attachment portion 70 of the extension against the interior of the body 34 of the stent graft 32 about the circumference of an aperture in the body 34 through which the tubular flow conduit 90 of the renal extension 52 (or 54) extends. Each renal extension 50 (or 52) generally includes a tubular body 60 having a proximal end 64, a generally cylindrical body 66 and a distal end 68, and an annular attachment portion 70, extending about the proximal end 64 of the renal extension 52. The tubular body 60 is, in this embodiment, comprised of a tubular segment of graft material 72, over which a stent frame 74, best shown in FIG. 5, is secured. As shown in FIG. 5, stent frame 74 includes a pair of stents 76, a, b, each of which may be configured of a wire material manipulated in a zigzag configuration and joined at its ends, such that a hoop diameter having a circumference slightly larger than that of the tubular portion of graft material 72 forming the generally cylindrical body 66 results. The stent frame 74 is sewn or otherwise affixed to the exterior of the tubular portion of the graft material 72, such that in a free state, where there is nothing restraining the expansion of the stent frame 74, the resulting diameter or circumference of the stent frame 74 is greater than a corresponding circumference or diameter of the renal artery 56. The stents 76a, b of the stent frame 74 may be manufactured from biocompatible stainless steel. Alternatively, the stents 76a, b may be formed by laser cutting tubes of shape memory material to create a wire-like zigzag patterned stent such as those shown as stents 76a, b or other known stent shapes.

Referring now FIGS. 3, 4 and 5 the attachment portion 70 of the renal extensions 50, 52 is in this embodiment configured as an annular disk shaped member 80 including a central aperture 82 to which the proximal end 64 of the tubular body 60 is attached such as will be described further herein, and an outer perimeter 121. As best shown in FIG. 5, the annular disk shaped member 80 may include a first annular disk element 84 formed from a substantially impermeable graft material, e.g., Dacron, PTFE, etc., having a centrally located hole 86 therethrough, a second annular disk element 88 configured from one of a hook material 90 (as shown in FIG. 7) or of a loop material 92 (Shown in FIG. 7) likewise having a second hole 94 therethrough, which is affixed, such as by sewing, to the first annular face 96 of the first annular disk element 84, to which an expansion member 98 is attached, such as by sewing the expansion member 98 to a second face 100 of the first annular disk element 84.

Figure 7:
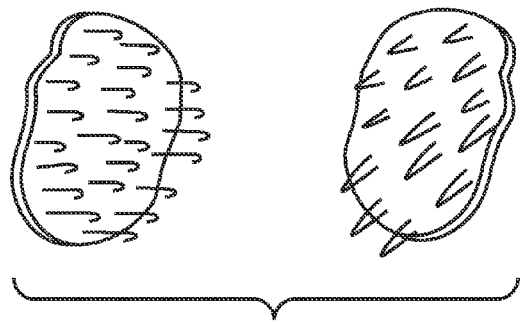
FIG. 7 consists of partial perspective views of examples of hook and loop materials useful for affixing the renal extension to the main body of the exclusion device.

As shown in FIG. 7, Hook material 91 and loop material 92 (a Velcro-like connection structure) are provided in sheet form, having a backing 102 of a biocompatible fabric, from which a plurality of individual hooks 104 or a plurality of individual loops 106 arch outward. By pressing the hooks against the loops, such as by pressing a sheet of a material having the loop portions looping outwardly therefrom against a sheet of material having the hooks extending outwardly therefrom, and then releasing the pushing force, a plurality of the hooks will become engaged through a plurality of the loops sufficient to hold the individual sheets of hook material 91 and loop material 92 together. To configure the second annular disk element 88, an annular ring of one of the hook material or the loop material is cut out, the annular ring being of the same general size as the first annular element 84 of graft material, which is then sewn to the first annular element.

Figure 6:
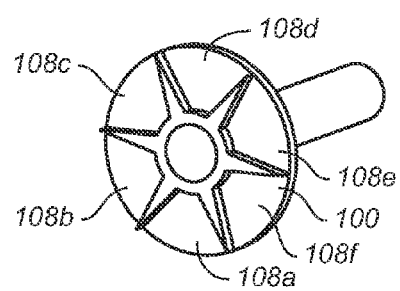
FIG. 6 is an isometric view of the reverse side of the renal extension shown in FIG. 4.

Referring back to FIG. 3, the expansion member 98 may be configured by laser cutting a sheet of shape memory material, such as Nitinol, to provide a shape which includes a generally centrally located ring portion 106 from which a plurality of individual spars 108, in this case six spars 108*a-f*, radiate outwardly (FIG. 6). The inner circumference 110 of the ring is sized to match the diameter of the hole 86 in first annular element 84. The expansion member 98 is attached to the second face 100 of the first annular element 84 such as by sewing it thereto.

Referring again to FIG. 3, the attachment portion 70 of the renal extension 52 includes hook material 91 as the second annular element 88, and a ring 114 of loop material 92 is secured to the graft material 36 of stent graft 32 and, in this embodiment, includes a central aperture 112 which defines the internal circumference of the aperture opening into which the renal extension 52 extends when deployed. Ring 114 includes both the central aperture 112 and an outer perimeter 116, along which perimeter 116 the ring 114 is sewn or otherwise affixed to the graft material 36 forming the body 34 of stent graft 32 using a sewing type or affixing arrangement. The outer perimeter 116 of the ring 114 may be circular, square, rectangular, etc, and the graft material 36 can include a mating profile graft aperture 118 into which the outer perimeter 116 closely fits for attachment thereto. Likewise, the outer perimeter 116 may be larger than the graft aperture 118 of the surrounding graft material 36, such that the expansion portion ring 114 overlaps the inner surface of the graft material 36 and is sewn thereto. Alternatively, the graft material 36 may be configured such that the graft aperture 118 is of the same diameter and geometry as the central aperture 112, and the ring 114 is again affixed to the inner surface of the of the graft material such that the graft aperture 118 and central aperture 112 are aligned, or the graft aperture 118 may be smaller in circumference than that of the ring central aperture 112, such that the inner perimeter of the graft aperture 118 defines the size of the aperture into which the renal extension 50 is located.

Figure 8:
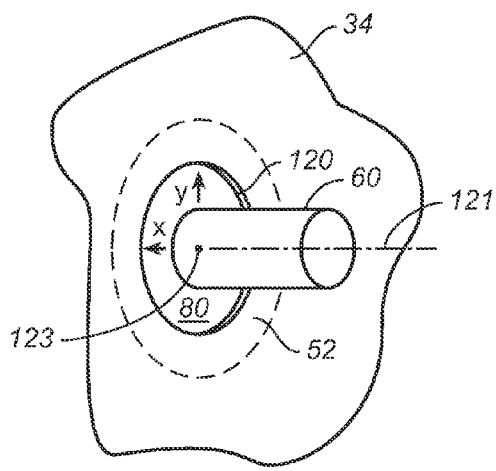
FIG. 8 is a partial perspective view of the renal extension deployed in the main body of the exclusion device of FIG. 2.
Figure 8A:
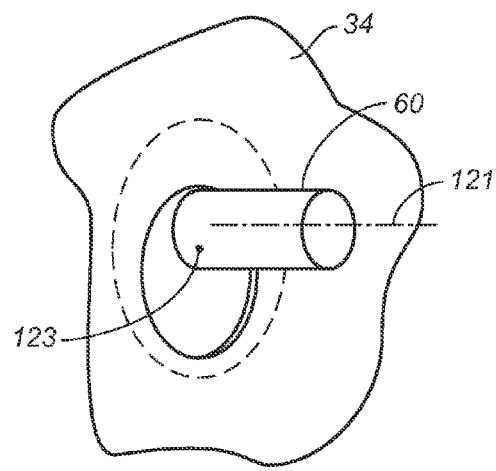
FIG. 8a is a partial perspective view of the renal extension deployed in the main body of the exclusion device of FIG. 2, wherein the position of the renal extension relative to the perimeter of an aperture in the main body of the stent graft is offset from the position of the renal extension therein shown in FIG. 8.

The central aperture 112 of the ring 114 and/or the graft aperture 118 inner perimeter where the ring 114 is affixed to the graft material 36 radially outwardly of the graft aperture 118, define the perimeter of an alignment aperture 120 into which the renal extension 52 (or 50) is deployed. The inner diameter of the alignment aperture 120 is larger than the outer diameter of the tubular body 60 of the renal extension 52, and thus the lateral center of the tubular body 60 defined by centerline 121 of the need not coincide with the center 123 of the aperture 120, but may be radially offset x and y coordinates (or radially offset from the center of the aperture 120) within the aperture 120, as shown in FIG. 8*a* as compared to the situation where the renal extension is centered in the aperture 120 as shown in FIG. 8. The diameter of the aperture 120 defines a profile area of the aperture, e.g., (pi×diameter$^2$/4), and the attachment portion 70 has a different, larger profile area, such that a portion of attachment portion is always overlying a portion of the body portion interiorly of the body portion 34 of the stent graft 32, to provide a sealing engagement between the renal extension 52 and the body portion 34. Thus, when deployed, the aperture 120 overlies the area where the renal artery 24 or 26 (only 26 shown in FIG. 3) exits from the aorta 10, but as the exit area of the renal artery 26 is substantially smaller than the profile area defined within the perimeter of aperture 120, the renal extension 52 may be aligned with the renal artery 26 without interference from the graft material 36 or the ring 114 where the ring extends inwardly from the perimeter of the graft material to define the perimeter of the aperture. Upon deployment, the tubular body 60 of the renal extension 52 is inserted into the renal artery 26, but it need not be centered within aperture 120. Thus, the relative sizes of the aperture 120 and the perimeter of the tubular body 60 provide an x-y (or radial) positional tolerance for the renal extension 52, vis-à-vis the positioning of the body 34 of the stent graft 32, with respect to the opening of the renal arteries 24, 26.

To ensure sealing of the aperture 120 and thus prevent blood leakage into the aneurysmal sac 18 (FIG. 2), the perimeter 121 of the attachment portion 80 is larger and of the same generally geometric configuration (Circular, square, ovoid, etc.) as the perimeter of the aperture 120, such that at the maximum tolerable center offset of deployment, where the tubular body 60 abuts the perimeter of the aperture 120, the face of the attachment portion 80 overlies the remaining area of the aperture 120 and extends further outward over the inner surface of the stent graft 32 to engage and seal against the ring 114. This maximum offset (extension) is generally on the order of at least one cm.

The stent graft 32 of this embodiment is a bifurcated stent graft, such that body 34 of the stent graft 30 includes, as shown in FIG. 2, a bifurcated main body 220 having a major diameter trunk 222 portion and a minor diameter first leg 224 extending from one end of the trunk 222, and a short second leg receiving portion 227 and terminating in an aperture 226 formed therein for receipt of a second leg 228. The second leg 228 is receivable within, and sealingly engageable against the inner surface of the main body 222, at the second leg aperture 226. To support the graft material 36 in an open tubular position when deployed into an aneurysmal descending aorta, a stent frame 40, comprised of stent frames 64, 64' (such as those shown in FIG. 9) are provided. Stent frame 64 is received over, and sewn to, main body 122, and stent frame 64' is received over, and sewn to, the second leg 128. In the embodiment shown the stent graft 32 has the general configuration of a Talent AAA Bifurcated Stent Graft sold by Medtronic Vascular, Inc. of Santa Rosa, Calif., except the upper portion of the trunk 222 thereof is modified to accommodate the renal extensions 50.

Figure 9:
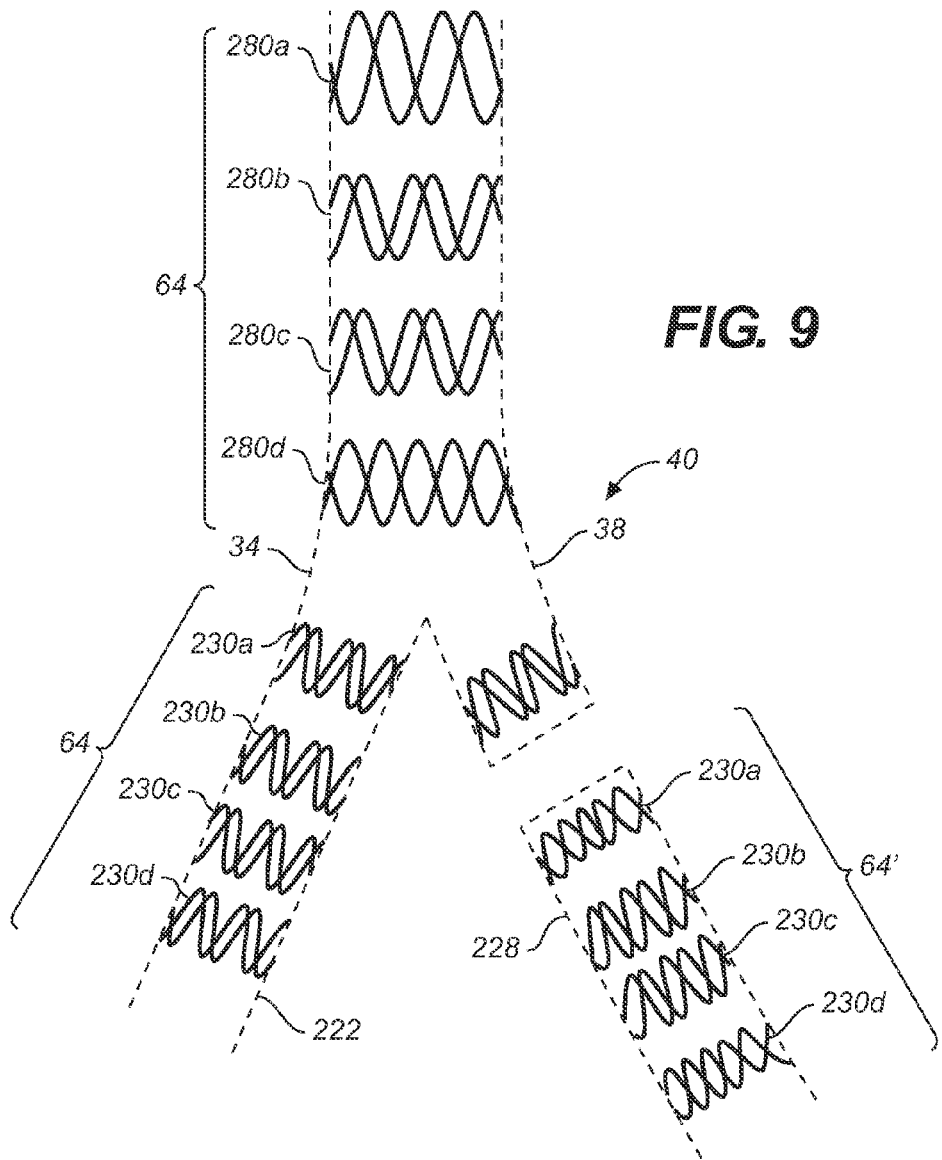
FIG. 9 is a plan view of a series of stents (which could be considered a framework) useful for supporting the exclusion device of FIG. 2.
Figure 10:
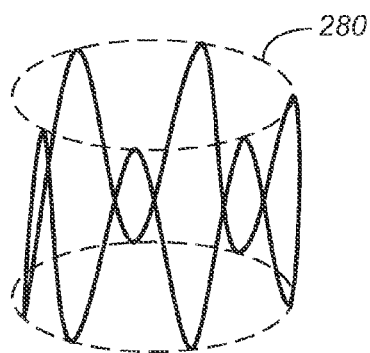
FIG. 10 is a perspective view of a stent of the stent framework of FIG. 9.

Referring now to FIGS. 9 and 10, each stent frame 64, 64' is comprised of a plurality of stent elements. Referring firstly to stent frame 64, this stent frame includes a plurality of stents 280*a-d* (A single one of which is shown in FIG. 9 in perspective) of a common free diameter slightly larger than the inner diameter of graft material 38 at trunk 222, as well as a plurality, in this embodiment four, smaller circumference leg stents 230*a-d* which are received over and sized with respect to leg 224. In this embodiment, only the most proximal and distal end leg stents 230*a-d* are connected by a connecting bar (not shown), as are the end stents of the main and leg portions. The middle stents are sewn to graft material between the end stents of the bifurcated body. Furthermore, leg stents 230*a-d* when deployed are also received over, and sewn to, the short leg 224 of main body 34.

Also, as is shown in FIG. 9, the stent frame 280 is shown as it will be positioned in the graft material 38, which is shown in dashed line phantom in the Figure. The stents 260 and 230 are sized and arranged to be received within the graft material 38, such that stents 260 and 230 will be slightly larger, in circumference (diameter), than the adjacent graft material into which they are deployed, such that they outwardly bias the graft material 38 to maintain the stent graft 32 as an open tubular structure. The stents 260 and 230 may also be deployed over the exterior of the graft material 38, and secured thereto by sewing of the stents 260 and 230 to the graft material 38. Additionally, a plurality of leg stents 230 are separately provided to form stent frame 64' for receipt within (or over) second leg 228 (also shown in phantom in FIG. 10). The uppermost leg stent 230a in second leg 228 is sized to ensure biasing of the second leg 228 graft material 38 into sealing engagement with the leg opening 226 in the main body 222, and the lowermost stents 230d in the legs 224, 228 are sized to bias the graft material of the legs 222, 228 adjacent their ends 45, 47 (FIG. 2) into sealing engagement with the adjacent aorta wall 12 as shown FIG. 2).

To form the trunk 222 and second leg 228 of stent graft 32, the stents making up the stent frames 64, 64' can be positioned within or outside the envelope of the graft portions making up the main body 222 and second leg 228. The stent frames 64, 64' are then sewn to the adjacent graft material 38, to secure the stent frames 64, 64' to the graft material 38 and form the components of the stent graft 32.

The material composing the graft material of the stent graft may be any biocompatible material that is mechanically stable in vivo, and is capable of preventing or substantially reducing the possibility of the passage or flow of blood or other body fluids there through. Typical materials for graft 24 include biocompatible plastics such as implantable quality woven polyester.

The material from which the stents are formed may be a shape memory material, such as Nitinol, which exhibits super elastic material properties. Alternatively, a material such as biocompatible stainless steel may be employed.

Figure 11:
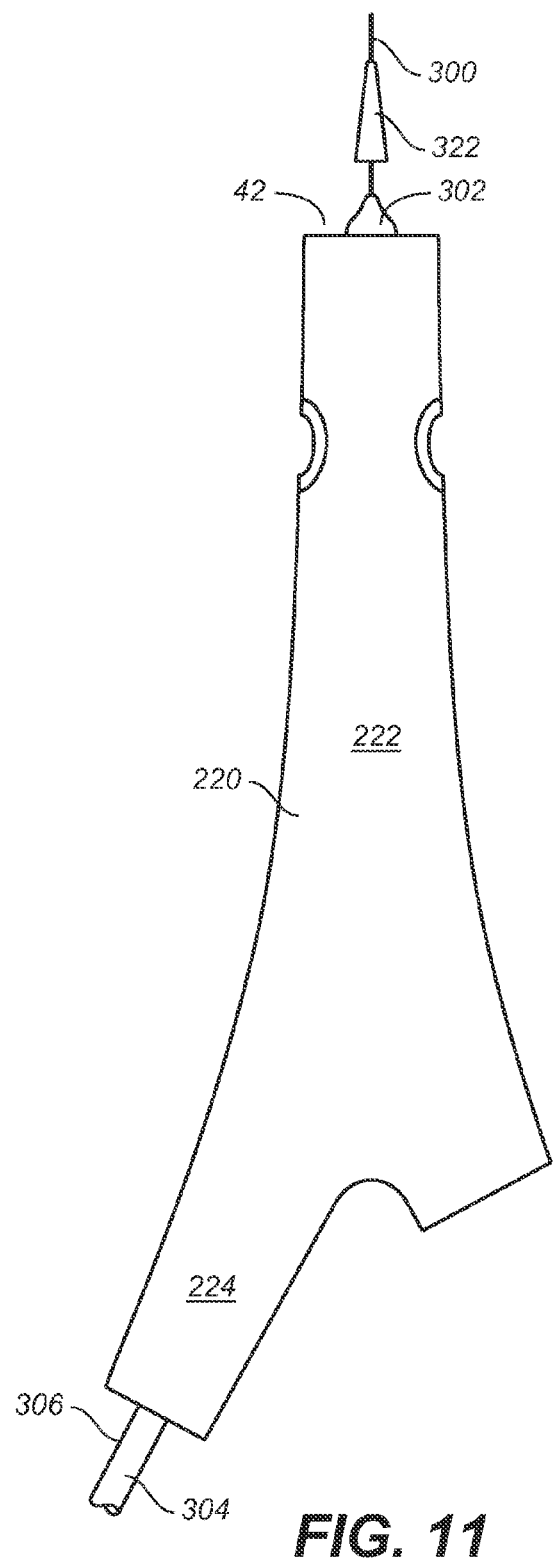
FIG. 11 is a plan view of a main body portion of an uncompressed configuration the exclusion device of FIG. 2.
Figure 12:
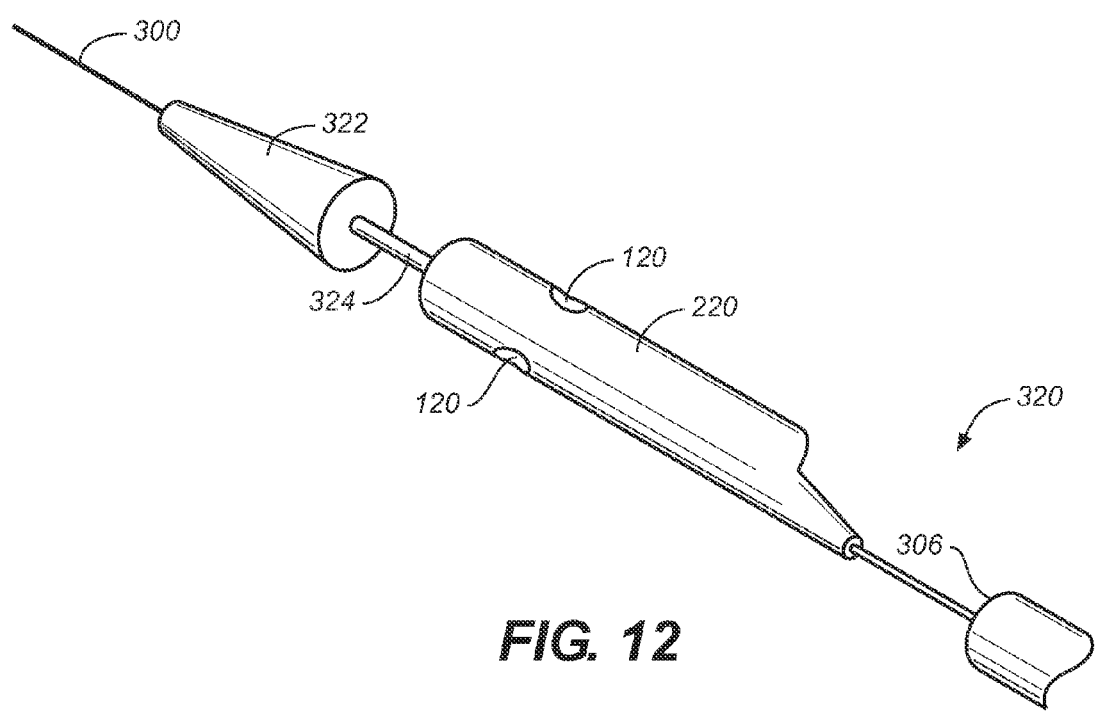
FIG. 12 is a perspective view of the main body portion of the exclusion device of FIG. 11, compressed prior to deployment into the delivery sheath of a catheter, for treatment of an abdominal aortic aneurysm.
Figure 13:
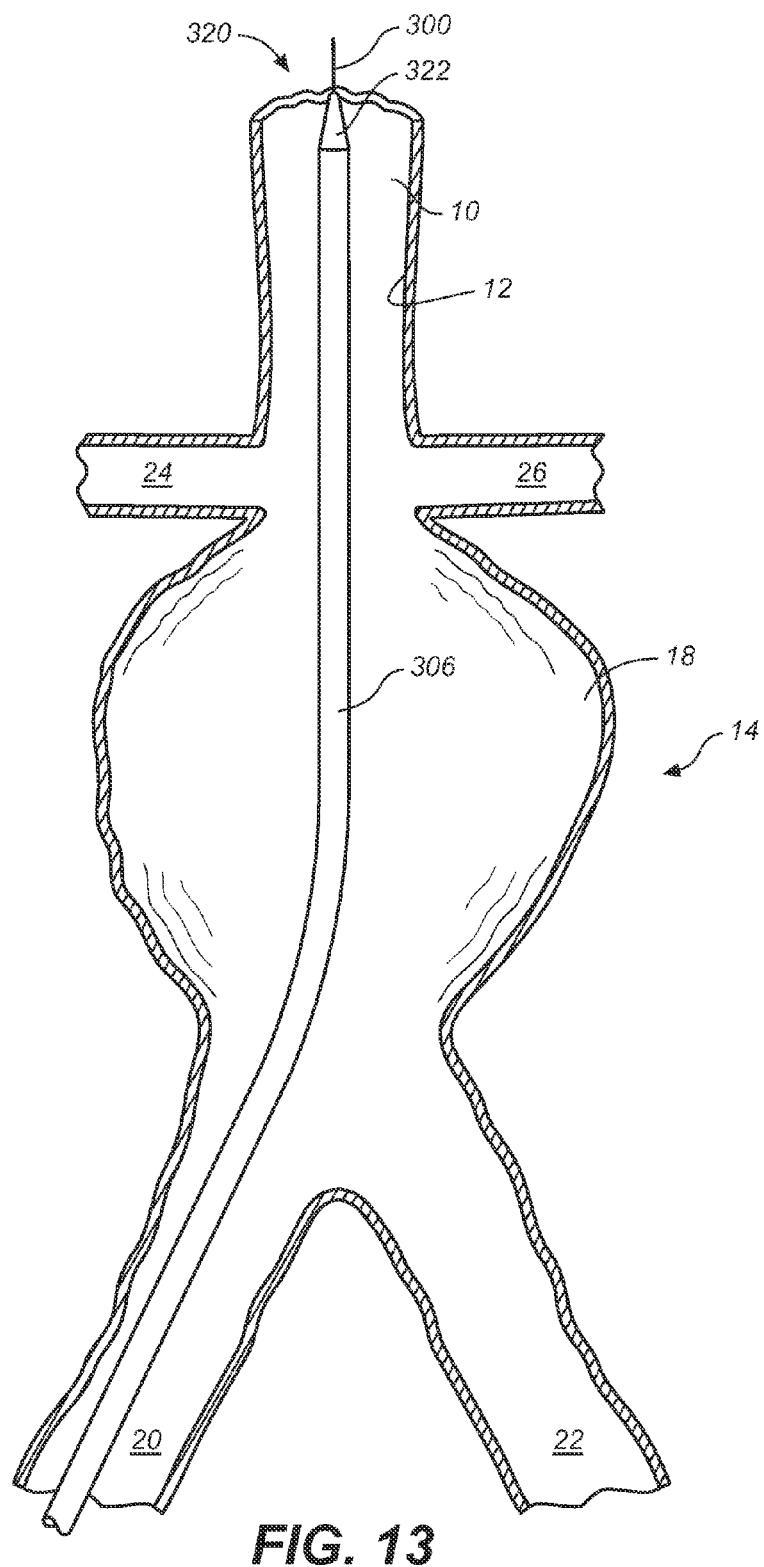
FIG. 13 is an artist's rendering of a cross section of an abdominal aortic aneurysm, showing a catheter, having the main body of an exclusion device therein for deployment across the aneurysmal region of the aorta, extending therethrough.

Referring now to FIGS. 11 through 18, the loading of the stent graft 32 into a deployment system and the deployment of the stent graft 32 is discussed. Referring initially to FIG. 11, the stent graft 32 is prepared for loading into a delivery system for the intravascular deployment thereof to an aneurismal aortic location. A tubular center (inner) member 304 having a guide wire lumen therethrough extends through the leg 224 of the main body portion 220 and through the trunk 222 and exits the proximal end 42 of the stent graft 32. A guidewire 300 that may be used to guide the inner member may include and have attached thereto, alternatively, a balloon 302 and an inflation tube 304 for the balloon 302. The center (inner) member 304 extends to a tip 322 of a catheter 320 (FIG. 12). The stent graft 32 main body 320 is then compressed, as shown in FIG. 12. As it is being compressed, the stent graft 32 main body 220 is surrounded by the open end of an advancing sheath 306, which is likewise a tubular member sized to receive the center member 304 and the compressed main body 220 of the stent graft 32 within the circumferential internal profile thereof. A similar operation is performed on second leg 228, and it is compressed within its own separate sheath 260. Additionally, the renal extensions 50, 52 are also placed loaded over center members with balloons, and compressed and placed into their own advancing delivery sheaths such as delivery sheath 356 shown in FIG. 17 for deploying renal extension 52 into renal artery 26.

To deploy the stent graft 32, incisions are first made into the leg iliac arteries of a patient. A guide catheter (not shown) containing a guide wire 300 is positioned in the aorta 10 and guided to a position beyond the deployment position for the stent graft 32. The guide catheter is removed and the stent graft catheter 320 is threaded over the guide wire. The stent graft catheter 320 is then introduced along the guidewire 300, the stent graft catheter 320 including the tapered introduction portion 322 which helps to pass the catheter 320 through slightly restricted locations along the artery. The stent graft catheter 320 is then introduced to the position shown in FIG. 13, above the deployment location for the stent graft. To locate the catheter 320, as well as the guide wire 300 and the stent graft 32 position vis-à-vis the aneurysmal region 14, the aneurysmal region 14 of the aorta 10 is radiologically marked, and the main body 320 of the stent graft 32 includes radiological marks thereon, such that the catheter 320, guidewire 300 and stent graft 32 may be fluoroscopically visualized by the practitioner deploying the stent graft 32.

Figure 14:
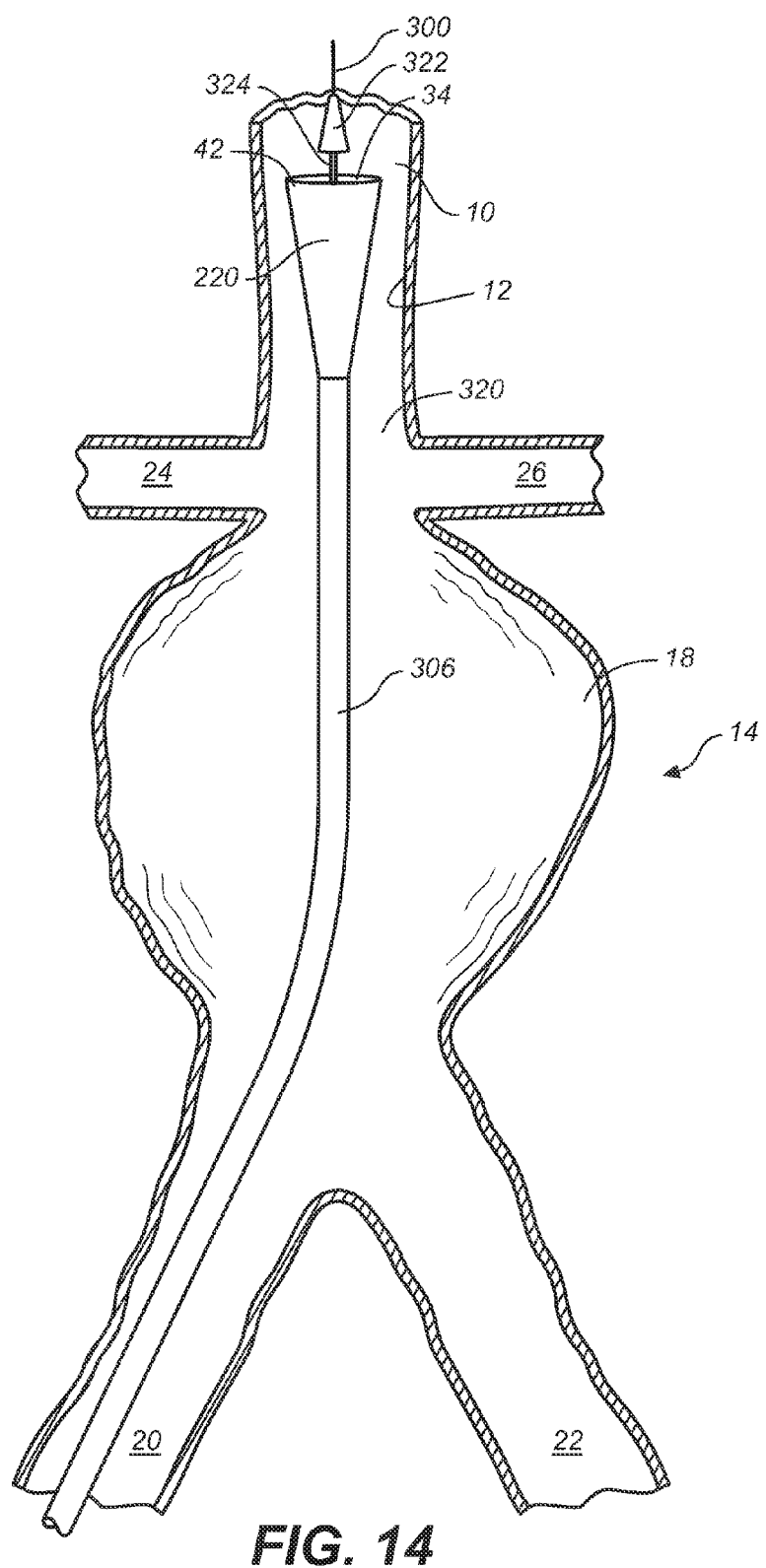
FIG. 14 is an artists rendering of a cross section of the abdominal aortic aneurysm of FIG. 13, showing the exclusion device starting to be deployed from the delivery catheter.
Figure 15:
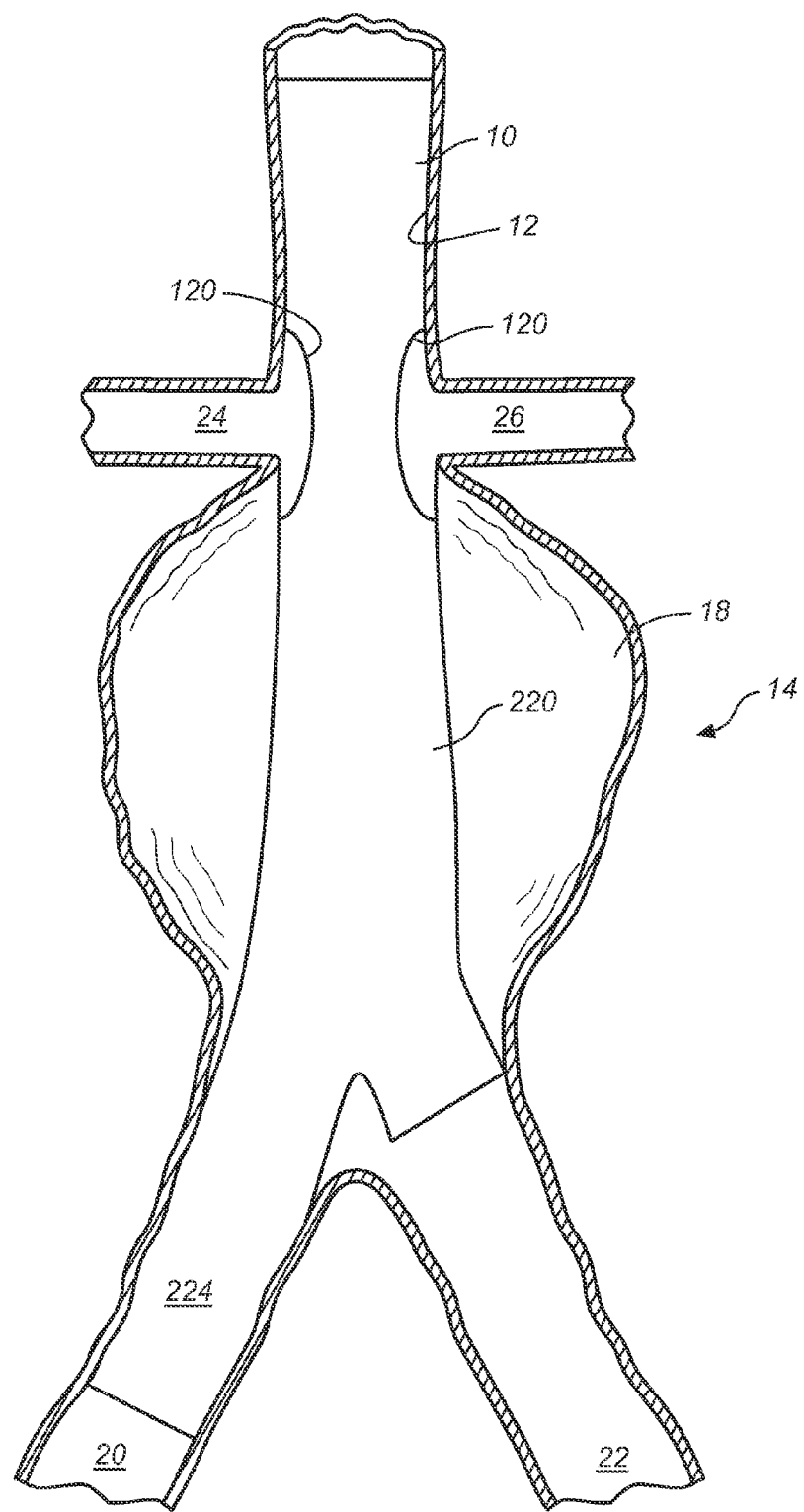
FIG. 15 is an artist's rendering of the aorta of FIG. 14, showing the main body portion (bifurcated stent graft) of the exclusion device deployed from the catheter and positioned to span the aneurysm.

Once the catheter 320 is properly positioned for deployment of the stent graft therefrom, the practitioner pulls back on the sheath 306, thereby separating the introduction portion 322 from the sheath 306 and thereby exposing the stent graft main body 220 (FIG. 14) within the catheter sheath 306. As shown in FIG. 14, the sheath 306 is then further retracted while a stop fixed to the inner member (not shown), maintains the position of the main body 220 as the catheter sheath 306 is retracted. As the catheter sheath 306 retracts, the proximal end 42 of the main body is released from the sheath 306, and the practitioner fluoroscopically views and may rotate the catheter 320 and sheath 306 to assure or enable alignment of apertures 120 (FIG. 15) for the renal extensions 50, 52 in alignment with the renal arteries 24, 26. Radiological markers are provided on the main body 220 to enable the practitioner to assess longitudinal and rotational position of the main body 220 as the main body 220 is deployed. The sheath 306 is then fully retracted to release the integral leg 224 within right iliac artery 20 as shown in FIG. 15. At this point the balloon 302 (FIG. 11) may, if needed, be inflated to grip the interior of the stent graft and press out any wrinkles which may have occurred during deployment. As the stent graft 32 is manufactured using a shape memory material as the stent material, the main body 220 and contra-lateral leg 228, when deployed, will attain their original shape prior to their being compressed for deployment. The balloon inflation can take place as the catheter is being removed. The center member 304 and tip 322 are drawn back into the sheath and the catheter 320 is removed.

Figure 16:
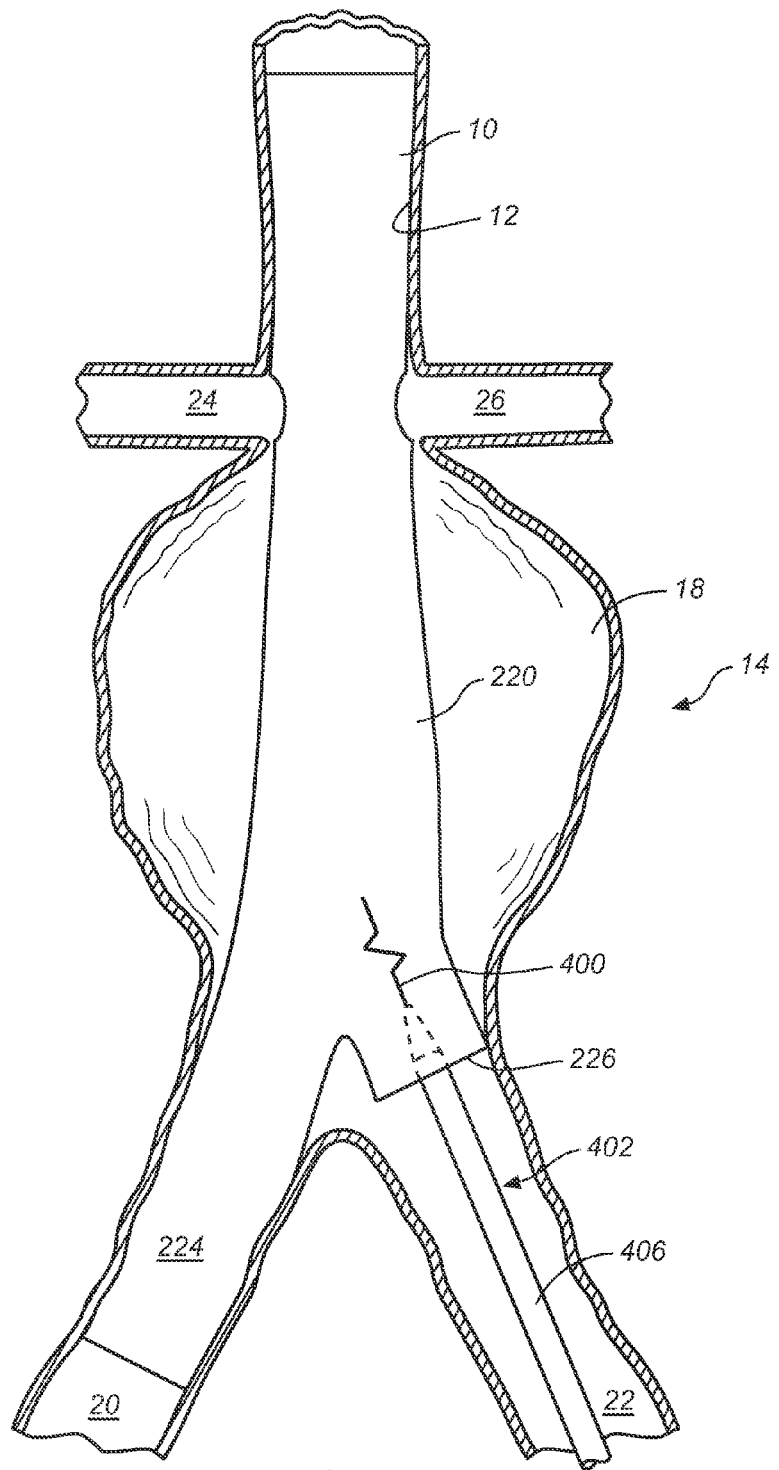
FIG. 16 is an artist's rendering of a cross section of an abdominal aortic aneurysm having the main body portion of the excluding device deployed therein, and a secondary deployment device catheter extending into the contra-lateral leg opening of the exclusion device.
Figure 17:
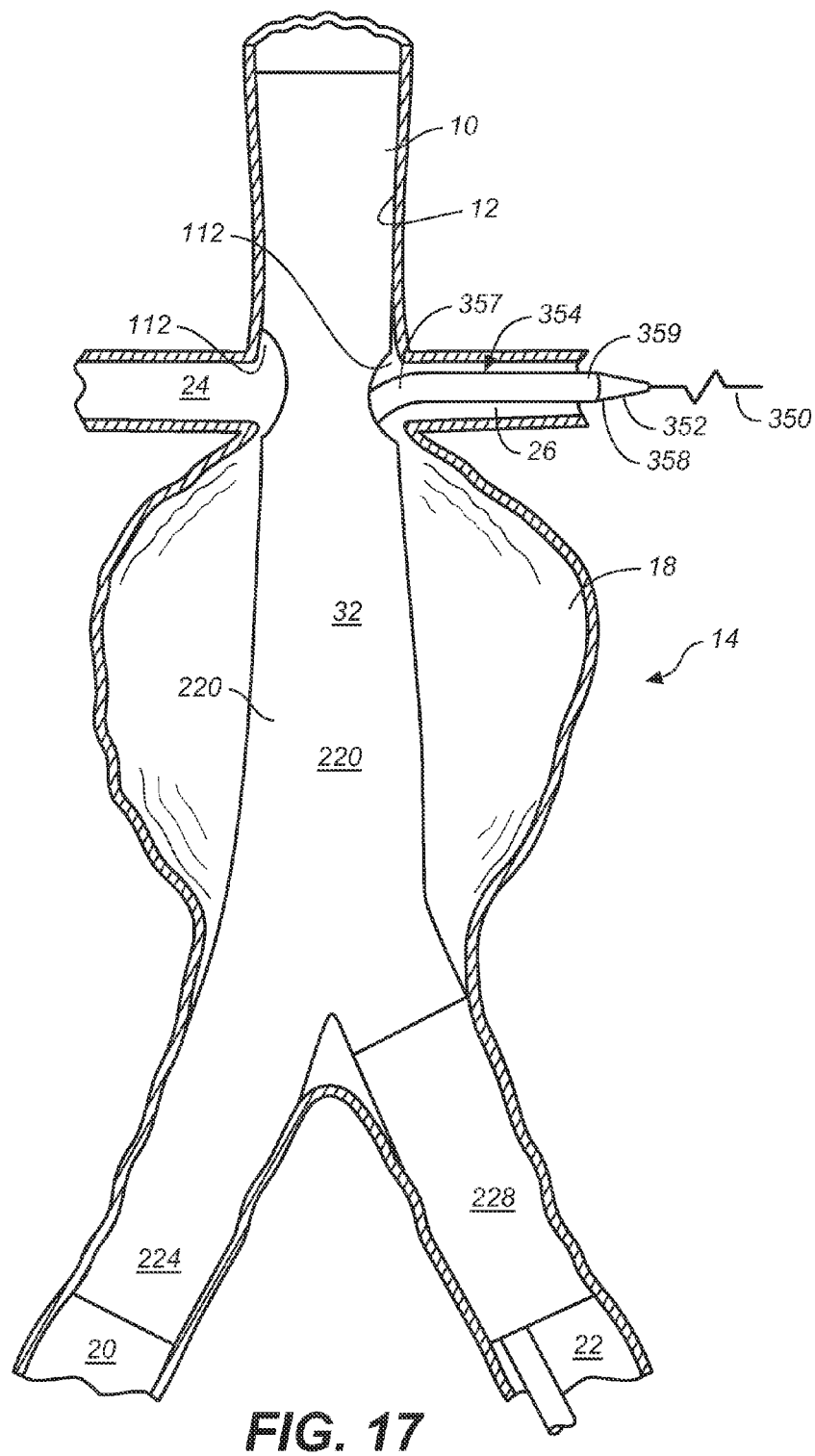
FIG. 17 is an artists rendering of a cross section of an abdominal aortic aneurysm having the main body of the excluding device deployed therein, and a secondary deployment catheter extending through the main body (bifurcated portion) of the exclusion device and out a side branch into a renal artery.

Once the main body 220 is deployed, the contra-lateral leg 228 may be deployed. To do so, a guidewire 400 is positioned within the main body portion 220, i.e., through the contra-lateral leg aperture 226. As shown in FIG. 16, a second catheter 402 holding the second leg 228 is fed along the guidewire 400, until it is positioned within the main body portion 220 as shown in phantom in FIG. 16. Then as was performed with the main body portion 220, a sheath 406 holding the contra-lateral leg 228 is retracted such that the proximal end of the leg is positioned in the leg aperture 226 and the distal end thereof seals against the wall of the left iliac artery 22 as shown in FIG. 17. A balloon catheter (not shown) may be introduced and inflated and used to remove any wrinkles in the second leg 228.

Referring still to FIG. 17, the main stent graft body 32 is deployed, but the renal extensions 50, 52 still remain to be deployed. Referring now to FIGS. 18 to 21, the deployment of renal extension 52 is shown, it being understood that a similar procedure may be used to deploy a second renal extension 50.

Figure 18:
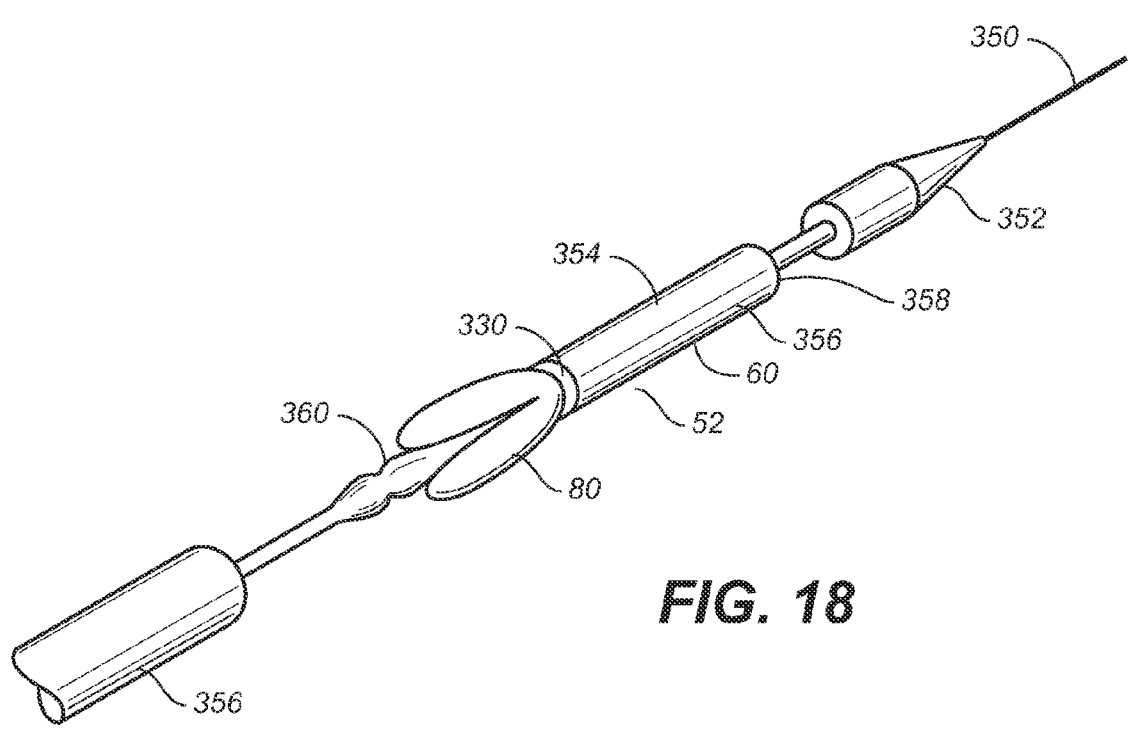
FIG. 18 is a perspective view of a portion of the secondary deployment catheter shown in FIG. 17, showing the arrangement of a renal extension prior to loading into the delivery device.

To prepare the renal extensions 50, 52 for deployment, they are where the stents 76 are Nitinol or other shape memory material, the stent first compressed as is shown in FIG. 18 for positioning inside of a delivery sheath 356 of deployment catheter 354. Specifically, during this procedure, the attachment portion 80 (a portion of attachment portion 70 seen in FIG. 5) of the renal extension 52 shown in FIG. 18 is folded away from the tubular body 60. The compressed renal extension 52 is then surrounded by the open end of the delivery sheath 356 for delivery of the renal extension 52 to the renal artery 26 location. Preferably, radiological markers 330 such as radiopaque tungsten are provided at the intersection or interconnection of the proximal end 64 of the tubular body 60 and attachment portion 70, such that, upon deployment, the location of this interface may be easily noticed under imaging while the compressed attachment portion 70 remains in the sheath such that the attachment portion 70 will be deployed within the body 34 of the stent graft 32.

Figure 19:
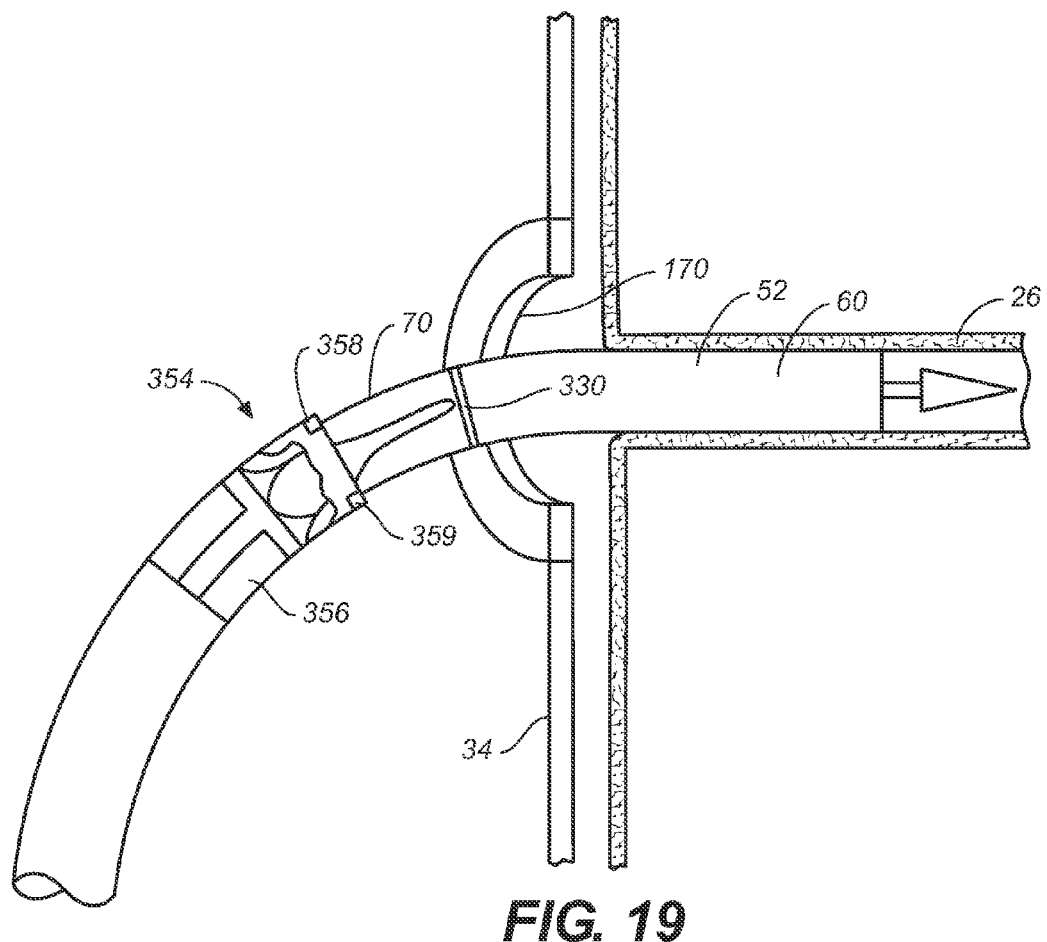
FIG. 19 is a partial side cut away view of the deployed portion of the exclusion device shown in FIG. 18, having the renal extension device partially deployed.

To deploy the renal extensions 52, initially, a guidewire 350 is conventionally positioned and guided into the interior of the stent graft 32 main body 220 and outwardly through an aperture 112 in main body 220 and into renal artery 26. The deployment of only renal extension 52 is discussed in detail, it being understood that a substantially similar procedure would be used to deploy renal extension 50. Once the guidewire 350 is located within the renal artery 26, a renal extension deployment catheter 354 is guided along the guidewire 350 to a position wherein the sheath holding the renal extension 60 extends into the renal artery 26 and is positioned such that the introduction portion 352 thereof is located beyond the deployment location of the renal extension 52 (FIG. 19). The location is determined by assessing the position of radiological markers such as radiopaque tungsten (not shown) on the deployment catheter 354, such that the position of the intersection of the tubular body 60 and the annular attachment portion will be deployed within the body 34 of the stent graft 32, so that the annular attachment portion 70 will open from its collapsed state adjacent to the inner wall of body 34 as will be described further herein. Thence, with the introduction portion 352 held relatively stationary, the delivery sheath 356 of catheter 354 is withdrawn from the renal; artery 26, while the renal extension is held relatively stationary therein by a stop 357 (shown in a cutaway of the delivery sheath 356) within delivery sheath 356, such that the tubular body 60 of the renal extension 52 will begin emerging from the end 358 of the sheath 356.

To properly position the delivery catheter 354 to ensure proper delivery of the renal extension 52, the distal end of the delivery sheath 356 into which the renal extension was loaded is positioned such that the location of the distal end 66 of the tubular body 60 of the renal extension 52 is fluoroscopically located at a position sufficiently inwardly of the renal artery 26. This position ensures sealing of the outer surface of the tubular body 60 against the inner wall of the renal artery 26. The intersection of the tubular body 60 and the annular attachment member 70 will be located inwardly of the body portion 34 of the stent graft 30 when the sheath 356 is fully retracted to release the renal extension 52. This is provided, in part, by locating radiological markers 359 on the end 358 of delivery sheath 356, and may also include a second such marker 357 (FIG. 17) inwardly of the end 358 of the delivery sheath 356 the indicative of the location of the intersection of the tubular body 60 portion of the renal extension with the annular attachment member 70 portion of the renal extension 52. This can be accomplished by x-raying of the sheath with the renal extension 52 therein, and ensuring alignment of this intersection previously marked by marker 330 on the renal extension with an additional radiological marker 357 inwardly of the end 358 of the sheath 356 aligned with the position of marker 330 on the renal extension 52.

As shown in FIG. 19, as the renal extension 52 is deploying, the tubular body 60 of the renal extension 52 is received in and is biased against the inner wall of renal artery 26 by self expansion of the stents 76a, 76b (FIG. 5), and the intersection of the tubular body 60 and attachment portion 70 which is radiologically marked at 330, is located within the body 34, i.e., to the inside side of the body 34 with respect to aperture 170. Additionally, the folded attachment portion 70 may be seen, in FIG. 19, as just about to be released from the delivery sheath 356 of delivery catheter 354. Further retraction of the delivery sheath 356 results in the release of annular attachment portion 70 from delivery sheath 356 as is shown in FIG. 20.

Figure 20:
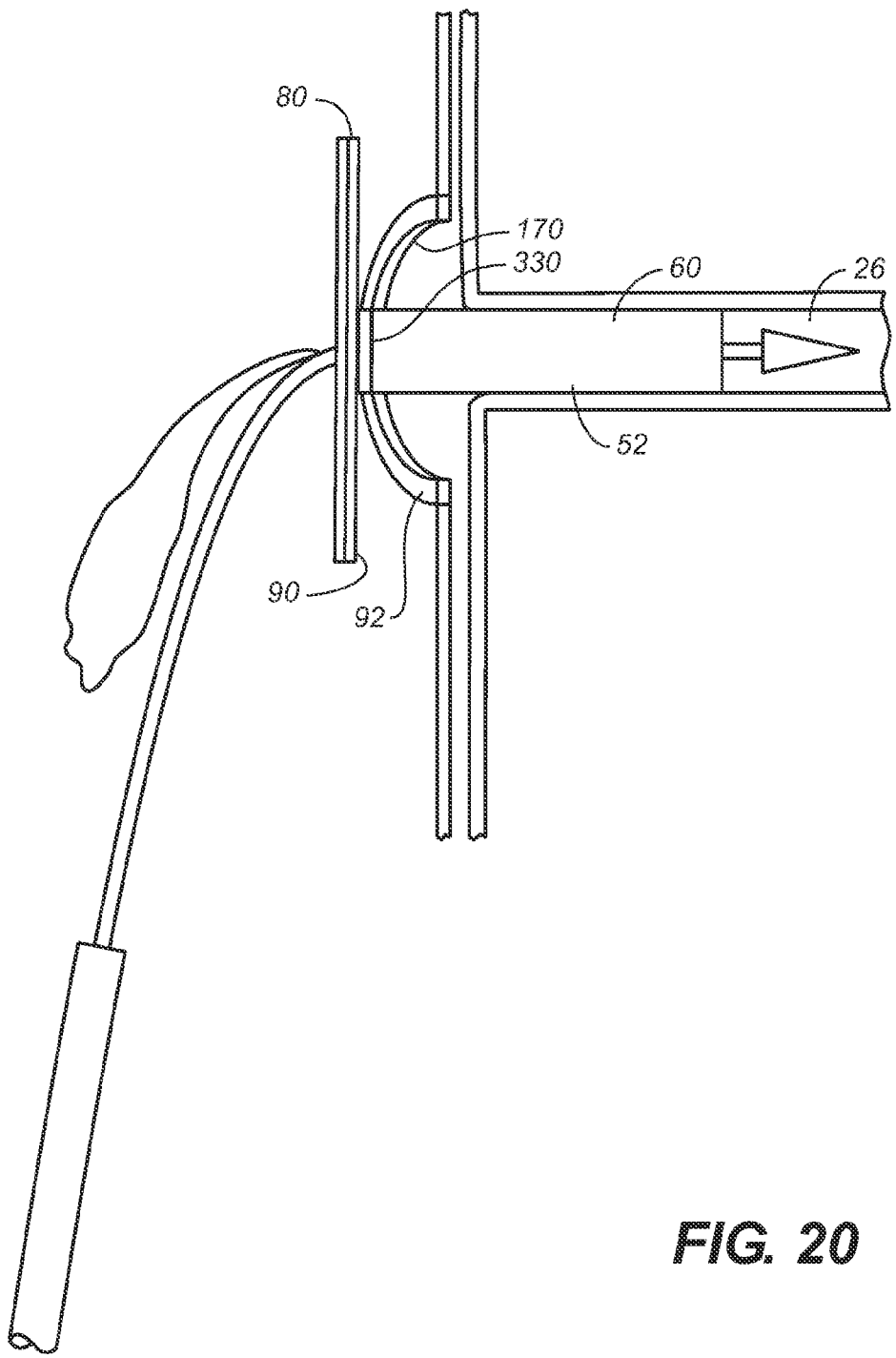
FIG. 20 is a partial side cut away view of the deployed portion of the exclusion device shown in FIG. 19, and further showing the renal extension deployed from a delivery device but prior to the affixation of the renal extension to the main body of the exclusion device.
Figure 21:
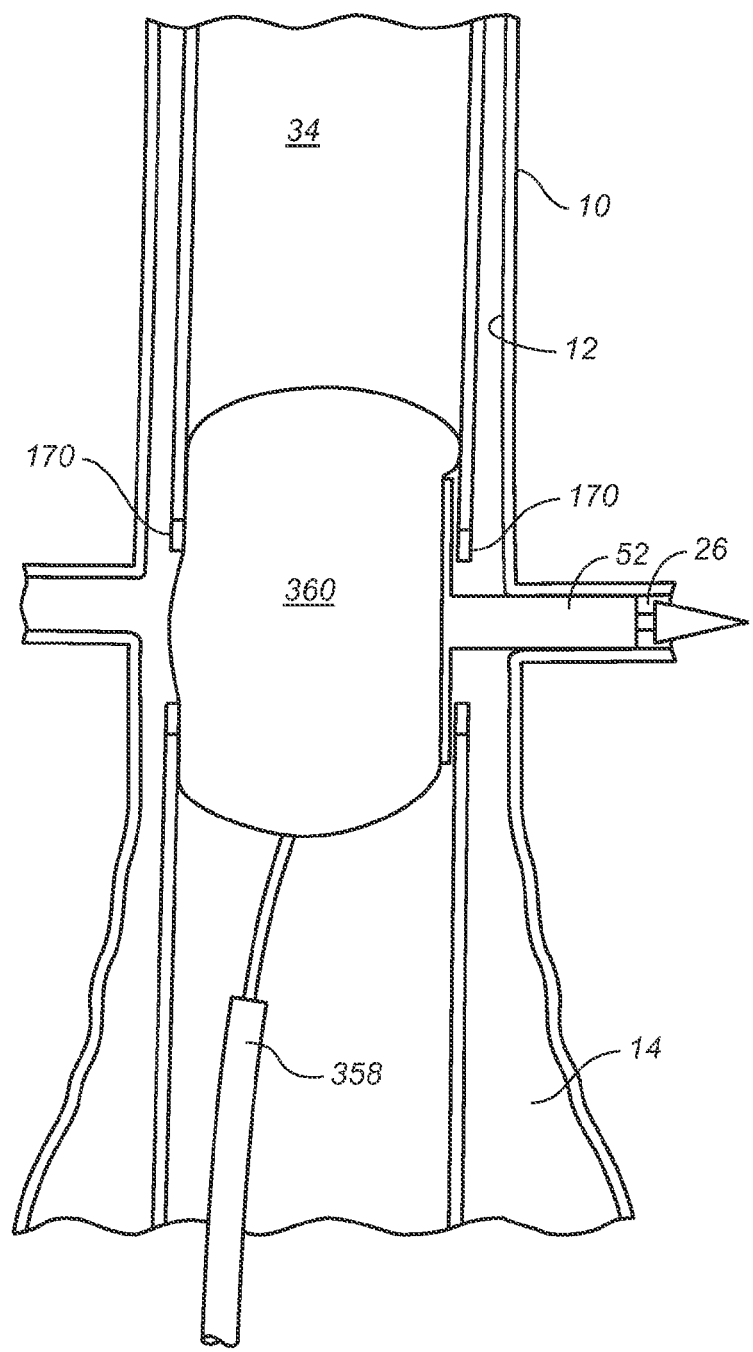
FIG. 21 is a partial side cut away view of the deployed portion of the exclusion device shown in FIG. 20, and further showing the renal extension pressed by an inflation balloon to be affixed to the main body of the exclusion device.

After the renal extension 52 is released, the tubular body 60 extends outwardly from the aperture 170 in body 34, and across any gap between the body 34 and adjacent aorta 10 wall 12, and is thence engaged against the inner wall 56 of the renal artery 26 adjacent distal end 66 thereof by the bias of the self expanding stents 76a, b, while the annular attachment portion 70 is located adjacent to, and spanning the perimeter or cross sectional area of the opening of, the aperture 170 as shown in FIG. 20. Because the aperture 170 is larger than the tubular body 60, the renal extension 52 is self aligning with the renal artery 26. To secure and seal the attachment portion 80 aperture 170 interface, a balloon 360 (as shown in FIGS. 20 and 21) is inflated within the main body 34 adjacent to the attachment portion 80, thereby causing the inflated balloon 360 to expand across the width of the body 34 adjacent to the aperture 170 (FIG. 21), enabling the balloon 360 to push the attachment portion 80 against the perimeter of the aperture 170 and against the side wall of the main body at the aperture 170, thereby causing the hook portions 90 and loop portions 92 (FIG. 7) to engage and lock together to secure the renal extension 52 in sealing engagement with the body 34 as shown in FIG. 21. The balloon 360 is deflated and removed.

The procedure is repeated for the deployment of the second renal extension 50, i.e., the renal extension 50 is loaded into a delivery catheter, the catheter is guided along a guidewire previously deployed into renal artery 24 such that the end of the delivery sheath within which the renal extension 50 is loaded is deployed through the aperture 170' adjacent renal artery and a distance into the renal artery as prescribed by the location of a radiological marker on the exterior of the delivery sheath indicative of the intersection of tubular body 60 and the annular attachment member 70' being located inwardly of the aperture of the body 34 of the stent graft. The delivery sheath is then retracted, such that the tubular body 60 engages against the inner surface of renal artery 24, and the annular attachment member is positioned adjacent to the aperture of the stent graft body 34. A second balloon is then inflated, to bias the annular attachment member of renal extension 50 into secured engagement against the hook or loop material about the perimeter of the aperture.

The stent graft 32 thus described provides a exclusion of blood to the aneurysmal sac 18, while enabling relatively easy deployment with less criticality of deployment location despite having the main body 34 of the stent graft 32 extend across branch arteries. This lessened criticality provides positional tolerance in both the linear deployment direction, i.e., the blood flow/reverse of blood flow direction, and the rotational direction, i.e., circumferentially at the aorta 10-renal artery 24, 26 interface. This decrease in positioning tolerance enables a multitude of advantages. For example, the stent graft 32 need not be completely customized to the patient, enabling rapid deployment of an existing stent graft 32 for patients in critical need for exclusion device deployment. It lessens the time for deployment of the stent graft 32, as the position of the stent graft is now not as critical vis-à-vis the renal or other branch arteries, and also reduces the level of skill needed by the practitioner to successfully deploy the stent graft.

What is claimed is:
1. An exclusion device for excluding fluid contact to an abnormality in a body flow lumen, comprising:
    a body portion having opposed open ends;

at least one aperture in said body portion located intermediate of said ends having a perimeter and a center location; and an extension configured to be positioned in said aperture and extending therefrom, said extension including an attachment portion receivable within said body portion and a tubular portion providing a secondary flow conduit from an interior of said body portion outwardly of said body portion, said attachment portion having a first profile area of a first size and having an outer perimeter, and a surface extending from an intersection of said tubular portion and said attachment portion to provide a sealing surface for engagement with an inner surface of said body portion;

wherein said aperture includes a second profile area of a second size that is larger than an outer perimeter of the tubular portion at the intersection with the tubular portion in an expanded configuration, and is smaller than said first size, such that with the tubular portion in the expanded configuration sealed against a branch vessel wall, a maximum center offset deployment, which occurs when the tubular portion abuts the perimeter of the aperture in one location of the aperture but is spaced from the aperture perimeter at another location of the aperture with the attachment portion overlying the remaining area of the aperture and extending further outward over the inner surface of the body portion to engage and seal against the inner surface, is at least one centimeter.

2. The exclusion device of claim 1, wherein said attachment portion includes a first securement material thereon.

3. The exclusion device of claim 2, wherein said body portion includes a generally hollow tubular portion, said aperture extends through said body portion, and said body portion includes, adjacent to said aperture, a second securement material complementary to said first securement material.

4. The exclusion device of claim 3, wherein one of said first and second securement material includes hooks and the other of said first and second securement material includes loops.

5. The exclusion device of claim 1, wherein said aperture is positionable about a branch flow lumen extending from a main flow lumen, and the position of the branch flow lumen with respect to the aperture may be varied.

6. The exclusion device of claim 1, wherein said attachment portion further includes a shape memory support member to maintain said attachment portion in a generally planar shape prior to the securement of said attachment portion to said body portion and spanning across said aperture.

7. The exclusion device of claim 3, wherein said aperture is formed within the second securement material.

8. The exclusion device of claim 7, wherein said exclusion device is a stent graft.

9. The exclusion device of claim 8, wherein said stent graft is a bifurcated stent graft and the body lumen is an aorta.

10. An exclusion device for excluding fluid contact to an abnormality in a body flow lumen, comprising:

a body portion having opposed open ends;

at least one aperture in said body portion located intermediate of said ends, said aperture having a center; and an extension configured to be positioned in said aperture and extending therefrom, said extension including an attachment portion receivable within said body portion and a tubular portion providing a flow conduit from an interior of said body portion outwardly of said body portion, said attachment portion having a first profile area of a first size that is larger than an outer perimeter of said tubular portion at an intersection of said attachment portion and said tubular portion;

wherein said aperture includes a second profile area of a second size that is larger than the outer perimeter of the tubular portion at the intersection with the tubular portion in an expanded configuration and is smaller than said first size and is sized such that an outer perimeter of said attachment portion extends against the interior of the body portion continuously about the aperture to seal the attachment portion of the extension within said aperture, wherein the maximum offset of said tubular portion with said tubular portion in the expanded configuration, which occurs when said tubular portion abuts the perimeter of said aperture in one location but is spaced from the perimeter of said aperture in another location, is at least one centimeter from the center of said aperture.

11. The exclusion device of claim 10, wherein said attachment portion includes a first securement material thereon: and said body portion includes a generally hollow tubular portion, said aperture extends through said body portion, and said body portion includes, adjacent to said aperture, a second securement material complementary to said first securement material.

12. The exclusion device of claim 11, wherein said aperture is positionable about a branch flow lumen extending from a main flow lumen, and the position of the branch flow lumen with respect to the aperture may be varied.

13. The exclusion device of claim 11, wherein said hollow tubular portion projects from said attachment portion, and the position of the intersection of the hollow body portion with respect to the aperture may be varied about the entire circumference of said intersection of the hollow body portion and said attachment portion.

14. The exclusion device of claim 13, wherein the exclusion device is a stent graft.

15. The exclusion device of claim 11, wherein upon deployment, said profile area is sized to fully cover a gap between the hollow tubular portion and said aperture.

* * * * *